United States Patent [19]

Kajfez

[11] 4,250,092
[45] Feb. 10, 1981

[54] DERIVATIVES OF N-CYANO-AZOMETHINES AND PROCESS FOR THEIR PREPARATION

[75] Inventor: Franjo Kajfez, Zagreb, Yugoslavia

[73] Assignee: CRC Compagnia di Ricerca Chimica S.A., Zurich, Switzerland

[21] Appl. No.: 38,838

[22] Filed: May 14, 1979

[30] Foreign Application Priority Data

May 12, 1978 [CH] Switzerland ............ 5237/78

[51] Int. Cl.³ .................................. C07C 125/08
[52] U.S. Cl. .................. 260/239 E; 564/106
[58] Field of Search .......... 260/239 E, 551 C

[56] References Cited

FOREIGN PATENT DOCUMENTS 46-41293 12/1971 Japan ............... 260/551 C
1253332 12/1971 United Kingdom .

Primary Examiner—Mark L. Berch
Attorney, Agent, or Firm—Haseltine and Lake

[57] ABSTRACT

N-Cyano-azomethines, useful as intermediates for the production of antihistamines are described. They are produced by reaction of

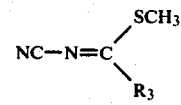

where $R_3$ is a thiomethyl group, an alkylamino group or N-1-amino-ω-alkylthiomethyl group, with primary or secondary alkyl- or hydroxyalkyl-amines or with ethylenimine.

4 Claims, No Drawings

DERIVATIVES OF N-CYANO-AZOMETHINES AND PROCESS FOR THEIR PREPARATION

The invention relates to new derivatives of N-cyano-azomethines of formula I

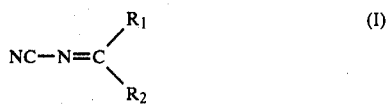

where $R_1$ denotes a —$SCH_3$ group, an N-amino-alkyl group, an N-dialkylamino group, an N-1-amino-alkyl-ω-thiomethyl group, or an N-1-amino-ω-hydroxy-alkyl group, wherein the hydroxy group can be esterified, all the alkyl groups having at most 4 carbon atoms in the chain, or an N-ethylenimino group, and $R_2$ has the same signification as $R_1$, provided that $R_1$ and $R_2$ are not both a methylthio or an N-ethylene-imino group, and a method for their production. Omega (ω) signifies that the hydroxyl group or thiomethyl group is at the end of the alkyl chain. The hydroxyl group may also be present in the form of a reactive ester.

The compounds of formula I are produced according to the invention by causing the reaction of compounds of the general formula II

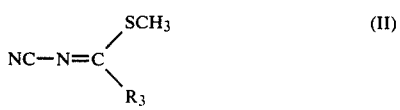

where $R_3$ denotes a thiomethyl group, an N-alkyl amino group, an N-1-amino-ω-alkylthiomethyl group wherein the alkyl group may contain at most 4 carbon atoms per chain, with corresponding primary or secondary ω-hydroxy-alkylamines with at most 4 carbon atoms per chain or with ethylenimine (aziridine). Omega (ω) has the same significance as in the definition of $R_2$.

When working with ethylenimine, one can obtain two different types of compounds of formula I; (1), the compounds resulting from the ring opening of ethylenimine which takes place under the influence of methylthiol liberated during the reaction, where $R_1$ or $R_2$ is equivalent to —$NHCH_2CH_2SCH_3$, or (2), the compounds with the ethylenimine ring unchanged. These compounds result if soluble salts of heavy metals, such as $AgNO_3$, $Pb(NO_3)_2$, $Zn(NO_3)_2$, etc. are present in the reaction mixture. These salts bind the resulting methylthiol, forming difficultly soluble deposits for which reason the ethylenimine ring remains unchanged. Because of the solubility of heavy metal salts, one preferably uses acetonitrile as solvent. However, one may also use solvents which can be used in the reaction in the absence of heavy metal salts and in the presence of bases, such as NaOH, KOH, $Et_3N$, etc.

If $R_3$ signifies an additional thiomethyl group, one can obtain asymmetrical compounds of the formula I directly in one step (one-pot method), by using two different alkylamines, or ω-hydroxy-alkylamines, i.e., one initially interchanges only one —$SCH_3$ group with the N-alkyl- or N-ω-hydroxy-alkyl group. The resulting compound is not isolated; rather, one causes the second —$SCH_3$ group to react with the second amino compound which differs from the first, in order to obtain the asymmetric compound of formula I. This reaction is done best in a low molecular weight (M.W.) alcohol, such as methanol, ethanol, isopropanol, butanol, pentanol, etc. For purely economic reasons, one preferably uses ethanol.

The same reaction can also be obtained with other solvents, such as acetonitrile, dimethyl sulfoxide, dimethyl formamide, etc; in these cases the reaction is very slow and the product isolated is a very impure red oil which crystallizes only with difficulty.

The best results are obtained when dissolving the amino compounds separately in a very low M.W. alcohol and then dripping this solution, while cooling, into the solution of compound II in a low M.W. alcohol. It was found that the initial compounds II easily oxidize in the presence of air, which leads to contaminated products. Better results are obtained when the reaction takes place in an inert atmosphere, for example in a continuous nitrogen flow. The initial compounds and the product compounds also are very sensitive to temperature. Therefore, the reaction is preferably performed between $-10°$ C. and $+20°$ C. With low temperatures, the reaction is very slow; at higher temperatures undesirable by-products reduce the yield and make the purification of the principal products of formula I difficult to achieve.

The compounds of formula I which have a free hydroxyl group can be converted into the reactive esters in a known manner. The esterification can be carried out, for example, with the chlorides of p-toluene sulfonic acid (p-tosyl group), p-bromobenzene sulfonic acid (p-brosyl group), or methanesulfonic acid (mesyl group). The best results are obtained by converting it to a tosyl ester with p-toluene sulfonic acid chloride in a known manner. All compounds described in the examples are new. Their identification was made according to the IUPAC nomenclature proposals of 1965, by which these compounds are considered as derivatives of azomethine:

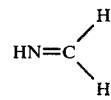

In this invention, the following new compounds were produced:

By Example 1: N-cyano-methylthio-2'-hydroxyethylamino-azomethine.

By Examples 2 to 4 and 7: N-cyanomethylamino-2'-hydroxyethylamino-azomethine.

By Example 5: N-cyanomethylthio-2'-thiomethylethylamino-azomethine.

By Example 6: N-cyano-methylamino-2-thiomethylamino-azomethine.

By Example 8: N-cyano-propylamino-2-hydroxyethylamino-azomethine.

By Example 9: N-cyano-methylamino-4-hydroxyamino-azomethine.

By Example 10: N-cyano-methylamino-2'-p-tosylethylamino-azomethine.

By Example 11: N-cyano-methylamino-ethyleneimino-azomethine.

By Example 12: N-cyano-methylamino-dimethylamino-azomethine.

By Example 13: N-cyano-methylthio-dimethylamino-azomethine.

By Example 14: N-cyano-bis-dimethylamino-azomethine.

The compounds of formula I are useful for the synthesis of pharmacologically active compounds, particularly antihistamines which act as H₂ receptor blockers.

The compounds of formula I especially the compound of example 11, are especially useful as intermediate products in the synthesis of compounds of formula III and IIIa $$\underset{\substack{N\\H}}{\overset{N}{\underset{\parallel}{\diagdown}}}\!\!\!\!\!\!\!\!\!\!\!\!\!\!\!\!\overset{\displaystyle CH_3}{\underset{\displaystyle CH_2-S-CH_2-CH_2-NH-\overset{N-C\equiv N}{\underset{\parallel}{C}}-NH-R}{\diagup}} \quad (III)$$

and (IIIa)

$$\underset{\substack{N\\H}}{\overset{N}{\underset{\parallel}{\diagdown}}}\!\!\!\!\!\!\!\!\!\!\!\!\overset{\displaystyle CH_3}{\underset{\displaystyle CH_2SH}{\diagup}} \quad \text{and} \quad (IV)$$

$$\underset{\substack{N\\H}}{\overset{N}{\underset{\parallel}{\diagdown}}}\!\!\!\!\!\!\!\!\!\!\!\!\overset{\displaystyle CH_2SH}{\underset{\displaystyle CH_3}{\diagup}} \quad (IVa)$$

disclosed in our copending U.S. application Ser. No. 038,836, filed May 14, 1979, now abandoned.

Compounds of formula III have been prepared by three different methods as disclosed in Drugs of the Future I, 1976, No. 1, page 13, and shown in chart I.

CHART I

[Chart I depicting the synthesis scheme with intermediate compounds, reagents (CH₃S)₂C=NCN, CH₃NCS, HS(CH₂)₂NH₂, CH₃NHC(=NCN)SCH₃, CH₃NH₂, NCNPb, and yields 80-90%, 90%]

As disclosed in Swiss Patent Application No. 10695/78 filed on Oct. 16, 1978 by CRC Compagnia di Ricerca Chimica S.A., of Chiasso, Switzerland, such compounds III and IIIa which are known antihistaminic compounds, are obtained by reacting the inventive compound of formula I with a new compound of formula IV or IVa These methods are further disclosed in the German Pat. No. 2,344,779 and in the U.S. Pat. No. 3,876,647 (left hand of Chart I); in French Pat. No. 2,199,467 (vertical part of Chart I), and Dutch Pat. No. 73.12198 (right hand of Chart I). All these known methods are using cysteamine hydrochloride (HS—CH₂CH₂—NH₂.HCl) as component and this compound is rather expensive. Contrary to the three known methods, the reaction of compound I with compound IV or IVa gives a nearly quantitative yield of 94 to 98%.

In order to explain the invention in more detail, several examples are cited below which, however, in no way limit the invention.

EXAMPLE 1

N-Cyano-methylthio-2'-hydroxyethylamino-azomethine

N'-Cyano-bis-methylthio-azomethine (10.0 grams, 0.068 mole) was dissolved in 100 ml of 99.8% ethanol. Under nitrogen flow and while stirring, a solution of 4.15 gram (0.068 mole) ethanolamine in ethanol was added dropwise over a 15 minute period. During the dropwise addition a white precipitate was formed. This was stirred for four hours at room temperature. The precipitate was removed by suction filtration, washed with ethanol, the filtrate was concentrated and the resulting precipitated product was added to the main quantity. 9.8 Grams (90.8% of the theoretical value) of the product was obtained with a melting point of 140° to 141° C. (decomposition), IR (KBr): 3250 (NH), 2160 (CN), 1570 (C=N), 1020. NMR (DMSO-$d_6$) : δ in ppm: 2.57 (s, 3H), 3.2 to 3.6 (m,4H), .4,2 to 5.3 (m,1H—OH), 7.5 to 8.7 (m,1H—NH).

Analysis for: $C_5H_9N_3O_S$. Calculated: C, 37.72; H, 5.70; N, 26.39%. Found: C, 38.00; H, 5.70; N, 26.13%.

EXAMPLE 2

N-Cyano-methylamino-2'-hydroxyethylamino-azomethine 5.44 Grams (0.0342 mole) of N-cyano-methylthio-2'-hydroxyethylamino-azomethine were suspended in 200 ml of 99.8% ethanol, cooled with water and exposed to a nitrogen flow, and an ethanol solution (73.6 ml) containing 10.6 grams (0.342 mole) of methylamine was added dropwise with stirring. This mixture was stirred at room temperature for another 5 hours, and then evaporated at reduced pressure until dry. There remained a colorless oil which crystallized when allowed to stand. The raw product was crystallized from 300 ml ethyl acetate and 10 ml acetone and 4.47 grams (92.1% of theoretical value) of product was obtained with a melting point of 109° to 110° C. After repeated recrystallization from the aforementioned solvent mixture, the product melted at 110° to 111° C. IR (KBr): 3260 (NH), 2155 (CN), 1600 (C=N), 1025 (CH). NMR (DMSO-$d_6$): δ in ppm: 2.68 (d,3H), 3.0 to 3.7 (m,4H), 4.79 (t,1H), 6.5 to 7.2 (m,2H—2NH).

Analysis for: $C_5H_{10}N_4O$ (142.15). Calculated: C, 42.24; H, 7.09; N, 39.42%. Found: C, 42.58; H, 7.11; N, 40.02%.

EXAMPLE 3

N-Cyano-methylamino-2'-hydroxyethylamino-azomethine 3.87 Grams (0.03 mole) of N-cyano-methylamino-methylthio-azomethine and 2.5 ml (2.44 grams, 0.4 mole) of ethanolamine was dissolved in 50 ml absolute alcohol and heated under reflux for about 20 hours. Then it was evaporated under the vacuum of a water jet pump and the oily residue (5.1 grams) was purified on a silica gel column (6120 silica gel). As elution agent, glacial acetic acid-acetone (4:1) was used and 0.410 grams (10.6%) of initial compound was obtained in the first fractions. Then 2.59 grams (59.1% of theoretical value) pure product was eluted, melting point: 97° to 98° C. After recrystallization from glacial acetic acid (with a little acetone) the melting point rose to 100°–101° C. After repeated crystallizing, the compound with the same properties as described in Example 2 was obtained.

EXAMPLE 4

N-Cyano-methylamino-2'-hydroxyethylamino-azomethine

The procedure is the same as in Example 3, but 200 ml acetonitrile was used as solvent. The ethanolamine, dissolved in the same solvent, was not added dropwise, but was mixed with N-cyano-methylamino-methylthio-azomethine. The reaction took place at 80° C.

However, the preparation of the above compound in acetonitrile was not satisfactory, since the reaction was slow and required reheating under reflux, so that an impure red oil was obtained. This oil crystallized partially and slowly when allowed to stand; but the separation of crystals was not successful.

Column chromatography, as performed in Example 3, only provided a 30% yield with a melting point of 97° to 98° C. After recrystallization from ethyl acetate, the product had a melting point of 100° to 101° C. and only after repeated recrystallization were the same properties as described in Example 2 obtained.

EXAMPLE 5

N-Cyano-methylthio-2'-thiomethylethylamino-azomethine

20 Grams (0.136 mole) of N-cyano-bis-thiomethyl-azomethine was dissolved in 250 ml of 99.8% ethanol and 7.1 ml (5.85 grams, 0.136 mole) of ethylenimine was added dropwise over a 15 minute period while stirring and cooling with ice. After 1 hour of stirring, the precipitate was removed by suction filtration and was rinsed with a small amount of ethanol. After partial evaporation of the mother liquor, a small amount of additional product was obtained. Total yield: 14.8 grams (57.6% of theoretical value). Melting point: 127° to 129° C. An analytically pure specimen was obtained after recrystallization from hot ethanol. Melting point: 129° to 130° C. IR (KBr): 3245 (NH), 2160 (CN), 1540 (C=N). NMR (CDCl$_3$): δ in ppm: 2.15 (s,3H—SCH$_3$ on the ethylene radical), 2.58 (s,3H), 2.75 (t,2H), 3.63 (q,2H), 7.0 to 7.5 (s,1H—NH).

Analysis for: $C_6H_{11}N_3S_2$ (189.30). Calculated: C, 38.06; H, 5.86; N, 22.20%. Found: C, 38.33; H, 5.93; N, 22.00%.

EXAMPLE 6

N-Cyano-methylamino-2'-thiomethylethylamino-azomethine

To 6.57 grams (0.03 mole) of N-cyano-thiomethyl-2'-thiomethylethylamino-azomethine suspended in 200 ml of 99.8% ethanol was added, dropwise, a 54. ml ethanol solution containing 9.3 grams (0.3 mole) of methylamine. The reaction mixture was then stirred for 20 hours at room temperature. After about 4 hours everything entered into solution. The solution was evaporated under reduced pressure until dry, with a thick light-brown oil (5.2 grams) remaining. When attempting to distill the under high vacuum, decomposition took place. The entire amount of raw product was purified on a silica gel column (180 grams silica gel) using glacial acetic acid as elution agent. In the first fractions 0.37 grams of initial compound was obtained. In later fractions the product obtained was a colorless oil in an amount of 4.81 grams (93.2% of theoretical value). IR (film): 3270 (NH), 2255 (CN), 1580 (C =N), NMR (acetone-d$_6$) δ in ppm: 2.12 (s,3H), 2.7 (q,2H), 2.86 (d,3H), 3.5 (q, 2H), 6.3 to 6.8 (wide s,2H).

Analysis for: C$_6$H$_{12}$N$_4$S (172.25). Calculated: C, 41.83; H, 7.02; N, 32.53%. Found: C, 42.02; H, 6.95; N, 32.40%.

EXAMPLE 7

N-Cyano-methylamino-2'-hydroxyethylamino-azomethine

This example described the one-pot procedure for the production of asymmetric compounds of the formula I. N-Cyano-bis-thiomethyl-azomethine (21.9 grams, 0.15 mole) was dissolved in 300 ml of 99.8% ethanol. To this solution was added, dropwise, 9.16 ml (0.15 mole) ethanolamine within 30 minutes while stirring and cooling with ice, and a colorless precipitate formed immediately. The reaction mixture was stirred for 4 hours at room temperature. Then an ethanolic solution of 15.5 grams (0.5 mole) of methylamine was dripped in over a 30 minute period but without cooling. Stirring was continued for another 18 hours at room temperature, with the entire precipitate again entering the solution. Evaporation of the solution until dry was effected. The light-yellow oily residue crystallized when allowed to stand. It was recrystallized from 250 ml glacial acetic acid and 10 ml acetone and 18.65 grams (87.5% of theoretical value) of product was obtained with a melting point between 100° to 108° C.

After once more recrystallization from glacial acetic acid a pure product with the same properties as stated in Example 2 was obtained.

EXAMPLE 8

N-Cyano-propylamino-2'-hydroxyethylamino-azomethine

Proceeding in the same manner as described in Example 7, but using 400 ml n-butanol as solvent and, instead of methylamine, a solution of 0.5 mole propylamine in 100 ml n-butanol was used, and the above titled compound was obtained with a yield of 90% of theoretical value. Melting point: 136° to 138° C.

EXAMPLE 9

N-Cyano-methylamino-4'-hydroxybutylamino-azomethine

Proceeding as directed in Example 7, but instead of ethanolamine, 0.2 mole of ω-butanolamine was added, dropwise, into the reaction mixture. The addition step proceeded at −10° C. The above titled compound was obtained in a 65% yield. Melting point: 146° to 148° C.

EXAMPLE 10

N-Cyano-methylamino-2'-p-tosylethylamino-azomethine 2.84 Grams (0.02 mole) of N-cyano-methylamino-2'-hydroxyethylamino-azomethine was dissolved in 28 ml dry pyridine, cooled to −5° C. and 5.72 grams (0.03 mole) of p-tosyl chloride was added gradually. The reaction mixture was stirred at a temperature between −1° C. and +1° C. for 2 hours, and 10 ml water was first added, dropwise, at temperatures below +5° C. and then another 120 ml of water was added at room temperature. After storing for a brief period in the refrigerator, the product crystallized. It was removed by suction filtration and washed with water. The product was dried in a desiccator over CaCl$_2$ and H$_2$SO$_4$ and 4.95 grams (87.8% of theoretical value) of the pure compound was obtained above with a melting point of 107° to 113° C. This product is unstable and should be used for further synthesis within 12 hours.

EXAMPLE 11

N-Cyano-methylamino-ethylenimine-azomethine 1.29 g (10 millimoles) of N-cyano-methylaminomethylthio-azomethine is added to 100 ml of acetonitrile and the suspension is cooled to −10° C. Then, in the following sequence, was added first, dropwise, 5.0 ml 2 N NaOH (10.0 millimoles) and then 5.0 ml ethylenimine. When everything was added, a clear solution resulted. Into this solution was added, dropwise, a solution of 1.699 grams (10.0 millimoles) of AgNO$_3$ in 15 ml acetonitrile over a 5 to 10 minute period, under intensive stirring. Soon a yellow deposit of silver methyl mercaptide started to precipitate. Stirring was continued for 2 hours while gradually increasing the temperature to 0° C. and for another 2 hours at room temperature. Then the precipitated silver salt was removed by suction, the filtrate was concentrated into a small volume and cooled. The product crystallized in the form of colorless prisms. Melting point: 123° to 124° C. R$_f$ =0.5 in a mixture of glacial acetic acid-acetone (5:2), IR (KBr) : 3250, 2160, 1595, 1545, 1410, 1380, 1372, 1275, 1190, 1155, 1060, 925 cm$^{-1}$. NMR (DMSO-d$_6$): δ in ppm: 2.32 (s,4H), 2.68 (s,3H), 7.8 to 8.2 (wide s, 1H).

Analysis for: C$_5$H$_8$N$_4$ (124.15). Calculated: C, 48.37; H, 6.49; N, 45.14%. Found: C, 49.00; H, 6.52; N, 45.22%.

EXAMPLE 12

N-Cyano-methylamino-dimethylamino-azomethine

Proceeding in the same manner as in Example 11, but instead of ethylenimine, dimethylamine was used, and instead of AgNO$_3$ the corresponding lead salt, Pb(NO$_3$)$_2$, was used, and the above titled compound was obtained with the following properties: crystallization from ethyl acetate, melting point: 125° to 126° C., IR (KBr): 3260 (NH), 2160 (C ≡N), 1580 (C =N) cm$^{-1}$. NMR (DMSO-d$_6$) : δ ppm: 2.85 (s,3H), 2.92 (s,6H).

Analysis for: C$_5$H$_{10}$N$_4$ (126.16). Calculated: C, 47.59; H, 7.99; N, 44.41%. Found: C, 47.41; H, 7.80; N, 44.56%.

EXAMPLE 13

N-Cyano-methylthio-dimethylamino-azomethine

Proceeding in the same manner as in Example 11, but starting with N-cyano-bis-dimethylthio-azomethine and dimethylamine in the presence of Ac Zn(CH$_3$COO)$_2$, the above titled compound was obtained with a yield of 95 to 98% and with the melting point 32° to 34° C. IR (KBr): 2170 (CN), 1580 (C =N). NMR (DMSO-d$_6$): δ in ppm: 2.63 (s,3H), 3.12 (s,6H).

Analysis for: C$_5$H$_9$N$_3$S (143.21). Calculated:; C, 41.93; H, 6.33; N, 29.34; S, 22.39%. Found: C, 42.19; H, 6.49; N, 29.07; S, 22.45%.

EXAMPLE 14

N-Cyano-bis-dimethylamino-azomethine 2.19 Grams (0.015 mole) of N-cyano-bis-thiomethyl-azomethine was dissolved in 50 ml of 99.8% ethanol and into this solution over a 30 minute period was added, dropwise, an ethanolic solution of 6.73 grams (0.15 mole) dimethylamine. The reaction mixture was initially stirred at room temperature for 2 hours and then at 60° to 65° C. for 70 hours. After evaporating the solvent an oily residue remained which was purified by high vacuum distillation. 1.58 Grams (75% of theoretical value) of the product was obtained with a melting point of 60 to 65° C./0.05 mm Hg. IR (film): 2160 (CN), 1530 (C=N), NMR (DMSO-$d_6$): δ in ppm:2.89 (s,12H).

Analysis for: $C_6H_{12}H_4$ (140.19). Calculated: C,51.40; H,8.63; N,39.97%. Found: C,51.22; H,8.29; N,39.49%.

What is claimed is:

1. N-Cyano-azomethines of formula I

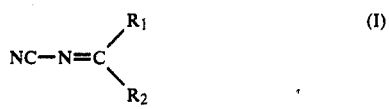

where $R_1$ denotes a —$SCH_3$ group, an alkylamino group, a dialkylamino group, an ω-thiomethylaklylamino group or an ω-hydroxyalkylamino group, and the tosylate, brosylate or mesylate derivatives thereof, all the alkyl groups having at most 4 carbon atoms in the chain, and omega (ω) signifying that the hydroxyl group or thiomethyl moiety of the thiomethylakylamino group is at the end of the alkyl chain, or an N-ethylene-imino group, and where $R_2$ is as defined for $R_1$ provided that $R_1$ and $R_2$ are not simultaneously a methylthio, alkylamino or an N-ethylene-imino group and $R_1$ is not alkylamino when $R_2$ is —$SCH_3$.

2. A compound as defined in claim 1, which is
N-cyano-methylthio-2'-hydroxyethylamino-azomethine,
N-cyano-methylamino-2'-hydroxyethylamino-azomethine,
N-cyano-methylthio-2-thiomethylethylamino-azomethine,
N-cyano-methylamino-2'-thiomethylehtylamino-azomethine,
N-cyano-propylamino-2'-hydroxyethylamino-azomethine,
N-cyano-methylamino-4'-hydroxybutylamino-azomethine,
N-cyano-methylamino-2'-p-tosylethylamino-azomethine,
N-cyano-methylamino-ethylene-imino-azomethine,
N-cyano-methylthio-dimethylamino-azomethine,
N-cyano-methylamino-dimethylamino-azomethine, or
N-cyano-bis-dimethylamino-azomethine.

3. An N-cyano-azomethine of formula I

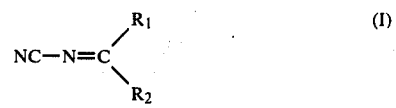

wherein $R_1$ denotes a—$SCH_3$ group, an alkylamino group, a dialkylamino group, an ω-thiomethylalkylamino group or an ω-hydroxyalkylamino group, and the tosylate, brosylate or mesylate derivatives thereof, all the alkyl groups having at most 4 carbon atoms in the chain, and omega (ω) signifying that the hydroxyl group or thiomethyl moiety of the thiomethylalkylamino group is at the end of the alkyl chain, and $R_2$ an N-ethylene-imino group.

4. A compound as defined in claim 3, which is N-cyano-methylamino-ethylene-imino-azomethine.